US012569440B2

(12) United States Patent
Wouters et al.

(10) Patent No.: US 12,569,440 B2
(45) Date of Patent: Mar. 10, 2026

(54) SOLID FORMULATION OF A 1,2,4-OXADIAZOLE DERIVATIVE

(71) Applicant: ABAXYS THERAPEUTICS, Villers-la-Ville (BE)

(72) Inventors: Johan Wouters, Namur (BE); Kalina Mambourg, Namur (BE); Francisco Javier Garcia-Ladona, Villers-la-Ville (BE)

(73) Assignee: ABAXYS THERAPEUTICS, Villers-la-Ville (BE)

( * ) Notice: Subject to any disclaimer, the term of this patent is extended or adjusted under 35 U.S.C. 154(b) by 925 days.

(21) Appl. No.: 17/627,309

(22) PCT Filed: Jul. 17, 2020

(86) PCT No.: PCT/EP2020/070307
§ 371 (c)(1),
(2) Date: Jan. 14, 2022

(87) PCT Pub. No.: WO2021/009355
PCT Pub. Date: Jan. 21, 2021

(65) Prior Publication Data
US 2022/0273572 A1 Sep. 1, 2022

(30) Foreign Application Priority Data
Jul. 18, 2019 (EP) .................................... 19187053

(51) Int. Cl.
*A61K 9/14* (2006.01)
*A61K 9/16* (2006.01)
*A61K 31/5377* (2006.01)

(52) U.S. Cl.
CPC ............ *A61K 9/145* (2013.01); *A61K 9/1682* (2013.01); *A61K 31/5377* (2013.01)

(58) Field of Classification Search
None
See application file for complete search history.

(56) References Cited

U.S. PATENT DOCUMENTS

2006/0240103 A1* 10/2006 McCallister ......... A61K 31/426 514/102
2014/0031347 A1* 1/2014 Rodriguez De Fonseca .............. A61K 31/4545 514/227.8

FOREIGN PATENT DOCUMENTS

WO 2012101292 A1 8/2012

OTHER PUBLICATIONS

Pubchem, ASN 15443627—Compound Summary, NCBI, CID 16677322, Aug. 17, 2007, 3 pages.
International Search Report mailed Oct. 16, 2020, in corresponding to International Application No. PCT/EP2020/070307; 3 pages.

* cited by examiner

*Primary Examiner* — Craig D Ricci
(74) *Attorney, Agent, or Firm* — Maier & Maier, PLLC

(57) ABSTRACT

A solid formulation including at least one 1,2,4-oxadiazole derivative of formula (I):

(I)

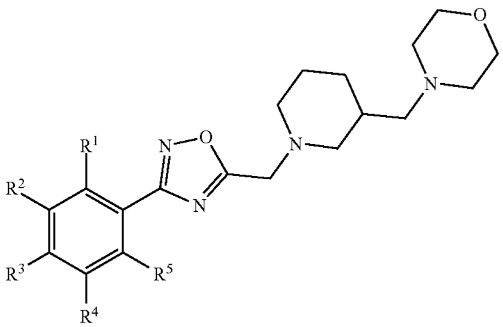

wherein $R^1$, $R^2$, $R^3$, $R^4$ and $R^5$ are each independently selected from hydrogen, $C_1$-$C_3$ alkyl, $C_1$-$C_3$ haloalkyl, $C_1$-$C_3$ alkoxy and $C_1$-$C_3$ thioalkyl; and citric acid and/or saccharin, wherein the molar ratio in the solid formulation between the total amount of citric acid and/or saccharin and the amount of the 1,2,4-oxadiazole derivative(s) ranges from about 2 to about 20. Also a process for manufacturing the solid composition and a method for increasing the physical stability of a 1,2,4-oxadiazole derivative of formula (I).

20 Claims, 4 Drawing Sheets

SOLID FORMULATION OF A 1,2,4-OXADIAZOLE DERIVATIVE

FIELD

The present invention relates to a solid formulation of a 1,2,4-oxadiazole derivative comprising exactly two monocyclic tertiary amine groups with citric acid and/or saccharin.

The present invention also relates to process for manufacturing a solid composition according to the invention comprising a step of mixing a 1,2,4-oxadiazole derivative comprising exactly two monocyclic tertiary amine groups with citric acid and/or saccharin; and to the solid formulation obtainable from the process.

The present invention also relates to a method for increasing the physical stability of a 1,2,4-oxadiazole derivative comprising exactly two monocyclic tertiary amine groups, comprising a step of mixing the 1,2,4-oxadiazole derivative with citric acid and/or saccharin.

BACKGROUND

Cardiometabolic diseases are among the most common causes of death in the world. They account for 32% of all deaths before cancer and chronic respiratory diseases, and effect more than 100 million people. It is predicted that it will cause more than 25 million deaths in 2030, compared to 17.5 million in 2005. It is estimated that in the United States, one in four adults is affected, whereas in Europe it affects 15% of adults.

A widespread cardiometabolic disorder is type 2 diabetes, or non-insulin-dependent diabetes. This diabetes is the most common form since it affects about 90% of people with diabetes. This disease affects all age groups but its frequency increases with age. For example, the incidence of the disease is 25% in the United States beyond 65 years; and over 75 years in France. At the global level, the incidence of diabetes among adults increased from 4.7% in 1980 to 8.5% in 2015. The mortality directly associated with diabetes is estimated at 1.6 million deaths per year. In addition, recent studies have shown that diabetes is associated, in 60% of cases, with the appearance of many other cardiometabolic risk factors such as hypertension, overweight and even obesity, and dyslipidaemia. The search for treatment for type 2 diabetes thus remains today a major challenge.

It is known that GLP-1 peptide receptor is involved in cardiovascular diseases and eating disorders such as diabetes, obesity or anorexia. Moreover, the GLP-1 receptor is also involved directly and indirectly in brain disorders, especially neurodegenerative disorders such as Alzheimer's disease, Parkinson's disease, psychiatric disorders such as schizophrenia and mood disorders. Thus, WO 2012/101292 A1 patent application (VIVIABIOTECH SL) discloses 1,2,4-oxadiazole derivatives for preventing and/or treating a disease in which GLP-1 receptor participates or mediates which may be useful in the treatment of diabetes.

However, the disclosed 1,2,4-oxadiazole derivatives are not convenient for widespread medical use as they present in the form of oils or deliquescent solids. Such physical forms are significant limitations for industrial manufacturing processes of drugs from these active ingredients because the oils or deliquescent solids are convenient neither for handling (transfer, mixing, cleaning) nor for quality control (e.g., in-line automated analyses), especially compared to homogeneous and stable liquids or powders. Storage between manufacture of the active ingredient and further manufacture of a pharmaceutical composition comprising it is also render more difficult with oils or deliquescent solids.

Therefore, it would be advantageous to obtain 1,2,4-oxadiazole derivatives as disclosed in WO 2012/101292 A1 in a more convenient physical form.

The Applicant carried out in-depth research in order to solve the technical problem of the physical stability of the 1,2,4-oxadiazole derivatives. Especially, it was tried to take advantage of the presence of tertiary amine functions in the 1,2,4-oxadiazole derivatives for manufacturing mono- or di-addition salts which may have to stabilized the intramolecular structure of the 1,2,4-oxadiazole derivative. Disappointingly, contacting an organic or inorganic acid with the 1,2,4-oxadiazole derivative lead in most cases to another sicky oil or to a hygroscopic solid which achieves quick deliquescence (as shown in the comparative Examples below). Therefore, it appeared that physically stable addition salts of the 1,2,4-oxadiazole derivatives cannot be easily formed.

However, the Applicant surprisingly found that a solid formulation may be obtained by mixing citric acid and/or saccharin with an 1,2,4-oxadiazole derivative comprising two monocyclic tertiary amine groups, and that the solid formulation manufactured thereby remained unexpectedly physically stable overtime.

SUMMARY

The invention relates to a solid formulation comprising from about 75% to about 100% w/w of:

at least one 1,2,4-oxadiazole derivative of formula (I):

(I)

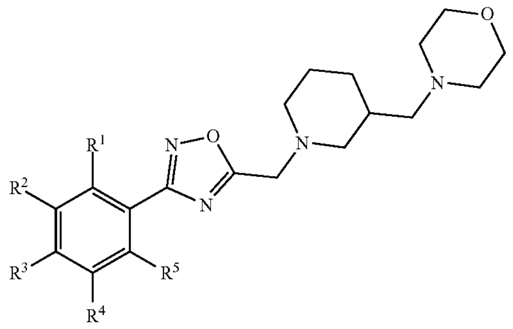

wherein $R^1$, $R^2$, $R^3$, $R^4$ and $R^5$ are each independently selected from hydrogen, $C_1$-C3 alkyl, $C_1$-$C_3$ haloalkyl, $C_1$-$C_3$ alkoxy and $C_1$-$C_3$ thioalkyl; and citric acid and/or saccharin, wherein the molar ratio in the solid formulation between the total amount of citric acid and/or saccharin and the amount of the 1,2,4-oxadiazole derivative(s) ranges from about 2 to about 20.

The invention also relates to a solid formulation obtainable by mixing: at least one 1,2,4-oxadiazole derivative as defined hereinabove with citric acid and/or saccharin, wherein the initial molar ratio between the total amount of citric acid and/or saccharin and the amount of the 1,2,4-oxadiazole derivative(s) ranges from about 2 to about 20, and wherein the solid formulation comprises a total amount of 1,2,4-oxadiazole derivative(s) and citric acid and/or saccharin ranging from about 75% to about 100% w/w.

According to one embodiment, $R^1$, $R^2$, $R^4$ and $R^5$ are hydrogen and $R^3$ is a $C_1$-$C_3$ haloalkyl; preferably a $C_1$-$C_3$ fluoroalkyl.

In one embodiment, the 1,2,4-oxadiazole derivative is the compound of formula (A):

(A)

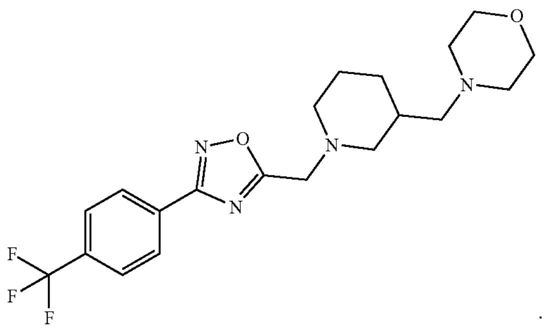

According to one embodiment, the molar ratio ranges from about 2 to about 10. In one embodiment, the molar ratio ranges from about 2 to about 5. In one specific embodiment, the molar ratio is about 2.

The invention also relates to a process for manufacturing a solid composition according to the invention comprising a step of mixing at least one 1,2,4-oxadiazole derivative as defined hereinabove with citric acid and/or saccharin, wherein the initial molar ratio between the total amount of citric acid and/or saccharin and the amount of the 1,2,4-oxadiazole derivative(s) ranges from about 2 to about 20; preferably ranges from about 2 to about 5.

The invention also relates to a method for increasing the physical stability of at least one 1,2,4-oxadiazole derivative as defined hereinabove, comprising a step of mixing the 1,2,4-oxadiazole derivative with citric acid and/or saccharin, wherein the initial molar ratio between the total amount of citric acid and/or saccharin and the amount of the 1,2,4-oxadiazole derivative(s) ranges from about 2 to about 20; preferably ranges from about 2 to about 5, and wherein no solvent is present during the mixing step. According to one embodiment, the mixing is stirring and/or grinding.

The invention also relates to a pharmaceutical composition comprising a solid formulation according to the invention and at least one pharmaceutically acceptable excipient. According to one embodiment, the at least one pharmaceutically acceptable excipient is free of citric acid and free of saccharin. The invention also relates to a solid formulation according to the invention or a pharmaceutical composition according to the invention for use as a medicament.

The invention also relates to a solid formulation according to the invention or a pharmaceutical composition according to the invention for use in the treatment and/or prevention of a disease in which GLP-1 receptor participates or mediates. According to one embodiment, the disease is selected from: metabolic disorders such as diabetes or obesity; diseases induced by or associated with metabolic disorders such as diabetic neuropathy, diabetic retinopathy, glaucoma, cataract, diabetic nephropathy or diabetic foot ulcer; cardiovascular diseases such as coronary artery diseases, stroke, heart failure, hypertensive heart disease or congenital heart disease; neurodegenerative diseases such as Alzheimer's disease, Parkinson's disease, multiple system atrophy, Huntington's disease, optic nerve degeneration and movement disorder, neuromuscular disorders or cognitive deficiency; and neurological or neuropsychiatric diseases such as epilepsy, schizophrenia, bipolar disorders, depression or pain.

DETAILED DESCRIPTION

Figure 1:
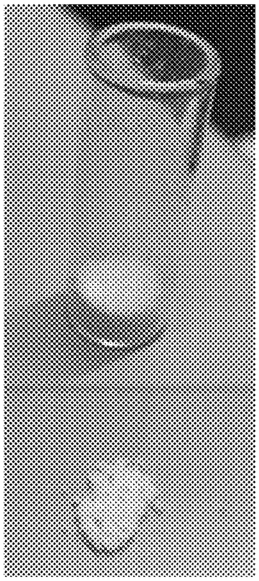
FIG. 1 is a photograph showing A-2CA as a physically stable white powder, obtained by grinding Compound A with 2.0 equivalents of citric acid.

In the present invention, the following terms have the following meanings:

- "About" preceding a figure means plus or less 10% of the value of said figure.
- "Alkoxy" refers to a group of formula -0-alkyl.
- "Alkyl" refers to any saturated linear or branched hydrocarbon chain with 1 to 12 carbon atoms; preferably 1 to 6 carbon atoms; more preferably 1 to 3 carbon atoms.

Examples of alkyl groups are methyl, ethyl, n-propyl, i-propyl, n-butyl, i-butyl, s-butyl, t-butyl, pentyl and its isomers (e.g. n-pentyl or i-pentyl), or hexyl and its isomers (e.g., n-hexyl or i-hexyl). Preferably, alkyl is ethyl or methyl; more preferably methyl.

- "Amine" refers to a group comprising the —$NH_2$ (primary amines), —NHR (secondary amines) or —NRR' (tertiary amines) functions, wherein R and R' are each different from hydrogen. Preferably, R and R' are independently alkyl groups Amines may be linear or ramified, alicyclic or cyclic (either monocyclic or polycyclic).
- "Deliquescence" refers to a process by which a solid substance absorbs ambient moisture ($H_2O$ present in the air) until it dissolves in the absorbed liquid to form a solution. Deliquescence occurs when the vapour pressure of the solution that is formed by absorption is lower than the partial pressure of water vapour in the air. A substance that absorbs moisture from the air to the point of dissolution is called "deliquescent". A substance that absorbs moisture from the air but not necessarily to the point of dissolution is called "hygroscopic".
- "Haloalkyl" refers to an alkyl group as defined hereinabove, wherein at least one hydrogen atom has been replaced by a halogen atom selected from fluoride, chloride, bromide and iodine. Preferably, each halogen atom in the haloalkyl is fluoride, i.e., the haloalkyl is a "fluoroalkyl".

"Hygroscopy" refers to a process by which a solid substance absorbs ambient moisture ($H_2O$ present in the air). If the substance finally dissolves in the absorbed liquid to form a solution, hygroscopy is called "deliquescence". A substance that absorbs moisture from the air but not necessarily to the point of dissolution is called "hygroscopic".

"Pharmaceutically acceptable" used in conjunction with an ingredient of a composition, it is meant that the ingredients of a pharmaceutical composition are compatible with each other and not deleterious to the subject to which the pharmaceutical composition is administered.

"Pharmaceutically acceptable excipient" refers to an excipient or vehicle that does not produce an adverse, allergic or other untoward reaction when administered to a subject, preferably a human. It includes any and all solvents, dispersion media, coatings, antibacterial and antifungal agents, isotonic and absorption delaying agents, and the like. For human administration, preparations should meet sterility, pyrogenicity, general safety and purity standards as required by regulatory offices, such as Food and Drug Administration (FDA) office or European Medicine Agency (EMA).

"Pharmaceutical composition" refers to a composition comprising at least a pharmaceutically active agent in association with at least a pharmaceutically acceptable excipient. A pharmaceutical composition is for therapeutic use, and relates to health. Especially, a pharmaceutical composition may be indicated for treating a disease selected from eating disorders, e.g., obesity.

"Physical stability" of a solid substance refers to the absence of deliquescence and melting of the substance at room temperature (about 20° C.) in the air. Melting of a solid substance is avoided when the melting point of the substance is higher than the ambient temperature. Physical stability is considered achieved when at least 90% w/w; preferably at least 95% w/w; more preferably at least 99% w/w; further more preferably at least 99.9% w/w; further more preferably at least 99.99% w/w, of the substance shows neither deliquescence nor melting. Preferably, hygroscopy of a physically stable substance should be low.

"Solid" refers to a substance whose melting point is higher than 25° C., at atmospheric pressure (1 atm, i.e., 101325 Pa).

"Specific surface area" refers to the total surface area of a substance per unit of mass ($m^2/g$). It can be measured, for instance, by BET (Brunauer, Emmett and Teller) analysis.

"Subject" refers to a warm-blooded animal, preferably a mammal, more preferably a human. Preferably, the subject is a patient, i.e., a subject who is awaiting the receipt of, or who is receiving medical care, or who is/will be the object of a medical procedure. For example, a subject may be treated for eating disorders, e.g., obesity.

"Therapeutic agent", "active agent" and "pharmaceutically active agent" are synonyms and refer to a compound for therapeutic use, and relates to health. Especially, a therapeutic agent may be indicated for treating eating disorders, e.g., obesity.

"Thioalkyl" refers to a group of formula-S-alkyl.

"Treating" or "treatment" or "alleviation" refers to both therapeutic treatment and prophylactic or preventative measures; wherein the object is to prevent or slow down (lessen) the targeted disease or condition in a subject in need thereof. Those in need of treatment include those already with the disease or condition as well as those prone to have the disorder or those in whom the disorder is to be prevented. A subject is successfully "treated" for a disease if, after receiving a therapeutic amount of an compound or composition according to the present invention, the subject shows observable and/or measurable reduction in or absence of one or more of the following: reduction in the number of pathogenic cells; reduction in the percent of total cells that are pathogenic; relief to some extent, of one or more of the symptoms associated with the specific disease or condition; reduced morbidity and mortality; and/or improvement in quality of life issues. The above parameters for assessing successful treatment and improvement in the disease are readily measurable by routine procedures familiar to a physician. For example, the disease may be selected from eating disorders, e.g., obesity.

DETAILED DESCRIPTION

Solid formulation

The invention relates to a solid formulation comprising:
- a 1,2,4-oxadiazole derivative comprising exactly two monocyclic tertiary amine groups and
- citric acid and/or saccharin,
- wherein the molar ratio in the solid formulation between the total amount of citric acid and/or saccharin and the amount of the 1,2,4-oxadiazole derivative is higher or equal to about 2.

The invention also relates to a solid formulation obtainable by mixing:
- a 1,2,4-oxadiazole derivative comprising exactly two monocyclic tertiary amine groups with
- citric acid and/or saccharin,
- wherein the initial molar ratio between the total amount of citric acid and/or saccharin and the amount of the 1,2,4-oxadiazole derivative is higher or equal to about 2.

According to one embodiment, no solvent is present during the mixing step. In one embodiment, no substance other than 1,2,4-oxadiazole derivative(s) and citric acid and/or saccharin is present during the mixing step.

According to one embodiment, the 1,2,4-oxadiazole derivative is a compound of formula (I-0):

(I-0)

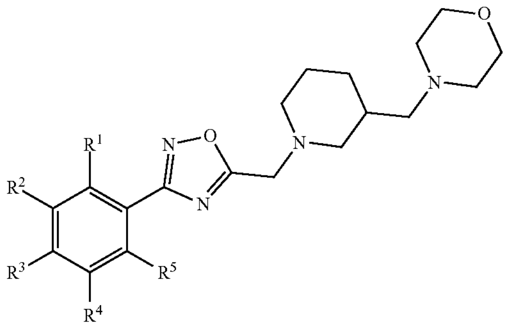

wherein $R^1$, $R^2$, $R^3$, $R^4$ and $R^5$ are each independently selected from hydrogen, $C_1$-C3 alkyl, $C_1$-$C_3$ haloalkyl, $C_1$-$C_3$ alkoxy and $C_1$-$C_3$ thioalkyl.

In one embodiment, $R^1$, $R^2$, $R^3$, $R^4$ and $R^5$ are each independently selected from hydrogen and $C_1$-$C_3$ haloalkyl; preferably the $C_1$-$C_3$ haloalkyl is a $C_1$-$C_3$ fluoroalkyl; more preferably a $C_1$-$C_3$ fluoroalkyl comprising exactly three fluoride atoms, such as trifluoromethyl. In one embodiment, $R^3$ is a $C_1$-C3 haloalkyl; preferably a $C_1$-$C_3$ fluoroalkyl; more preferably a $C_1$-$C_3$ fluoroalkyl comprising exactly three fluoride atoms, such as trifluoromethyl.

In one embodiment, at least two among $R^1$, $R^2$, $R^3$, $R^4$ and $R^5$ are hydrogen. In one specific embodiment, $R^1$ and $R^5$ are hydrogen. In one embodiment, at least four among $R^1$, $R^2$, $R^3$, $R^4$ and $R^5$ are hydrogen. In one specific embodiment, $R^1$, $R^2$, $R^4$ and $R^5$ are hydrogen.

In one preferred embodiment, the 1,2,4-oxadiazole derivative is 44(14(344-(trifluoromethyl)phenyl)-1,2,4-oxadiazol-5-yl)methyl)piperidin-3-yl)methyl)morpholine of formula (A) (hereafter "Compound A"):

(A)

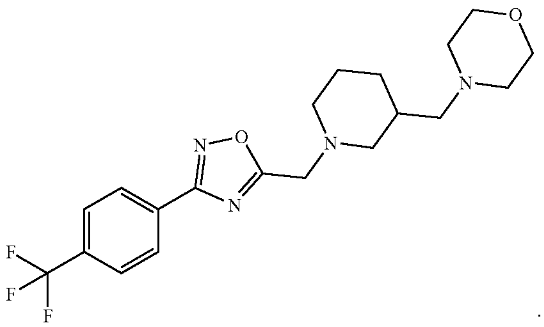

.

Compound A was named using ChemDraw Professional 15.0 (PerkinElmer).

Citric acid or "2-Hydroxypropane-1,2,3-tricarboxylic acid" ($C_6H_8O_7$, CAS [77-92-9]) of formula:

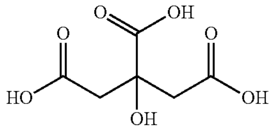 [SMILES: O=C(O)CC(O)(CC(=O)O)C(=O)O]

is a weak organic acid (pKa for acid groups of 5.2, 4.3 and 3.0 at 25° C.) occurring naturally in citrus fruits.

Saccharin or "benzoic sulfimide" or "1,1-dioxo-1,2-benzothiazol-3-one" (C7H5NO3S, CAS [81-07-2]) of formula:

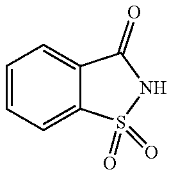 [SMILES: O=C1NS(=O)(=O)c2ccccc21]

is a weak organic acid ($pK_a$ of 1.6 at 25° C.) manufactured with synthetic chemistry.

Any reference to "1,2,4-oxadiazole derivative", "citric acid" or "saccharin" in the present disclosure encompass any enantiomers and solvates thereof. Any reference to "1,2,4-oxadiazole derivative", "citric acid" or "saccharin" in the present disclosure encompass any salts thereof, preferably pharmaceutically acceptable salts thereof. Any reference to "a compound" (e.g., "a 1,2,4-oxadiazole derivative") should be constructed as meaning "at least one compound" and thus encompasses any mixtures of two or more 1,2,4-oxadiazole derivatives, enantiomers, solvates and/or salts thereof.

According to one embodiment, the solid formulation comprises about 50% w/w or more of 1,2,4-oxadiazole derivative(s) and citric acid and/or saccharin (i.e., the total amount of 1,2,4-oxadiazole derivative(s) and citric acid and/or saccharin represents at least about 50% of the total weight of the solid composition). In one embodiment, the solid formulation comprises a total amount of 1,2,4-oxadiazole derivative(s) and citric acid and/or saccharin ranging from about 75% to about 100% w/w, preferably ranging from about 85% to 99% w/w, more preferably ranging from about 90% to 98% w/w, furthermore preferably ranging from about 95% to 97% w/w, furthermore preferably ranging from about 95% to 96% w/w. In these embodiments, "w/w" means "in weight of the total weight of the solid formulation". In one embodiment, the solid formulation consists of 1,2,4-oxadiazole derivative(s) and citric acid and/or saccharin.

According to one embodiment, the solid formulation comprises a mono- or di-citrate salt of the 1,2,4-oxadiazole derivative. In one embodiment, the solid formulation comprises a di-citrate salt of the 1,2,4-oxadiazole derivative. According to one embodiment, the solid formulation comprises a mono- or di-saccharin salt of the 1,2,4-oxadiazole derivative. In one embodiment, the solid formulation comprises a di-saccharin salt of the 1,2,4-oxadiazole derivative. In one embodiment, the solid formulation comprises a mono-citrate and mono-saccharin salt of the 1,2,4-oxadiazole derivative.

In one embodiment, the solid formulation comprises or consists of:

the 1,2,4-oxadiazole derivative and/or a salt thereof, and (citric acid and/or a salt thereof) and/or (saccharin and/or a salt thereof).

According to one embodiment, the molar ratio in the solid formulation or the initial molar ratio between the total amount of citric acid and/or saccharin and the amount of the 1,2,4-oxadiazole derivative is lower or equal to about 100. In one embodiment, the molar ratio ranges from about 2 to about 20. In one specific embodiment, the molar ratio ranges from about 2 to about 10. In one further specific embodiment, the molar ratio ranges from about 2 to about 5. In one further specific embodiment, the molar ratio is about 2, about 3, about 4 or about 5. In one further specific embodiment, the molar ratio ranges from about 2 to about 3. In one further specific embodiment, the molar ratio is about 2.

According to one embodiment, the solid formulation keeps its physical stability (as defined hereinabove) for at least 7 days at 19±2° C. and 60±5% humidity. In one embodiment, the solid formulation keeps its physical stability for at least 12 days. In one specific embodiment, the solid formulation keeps its physical stability for at least 2 weeks. In one further specific embodiment, the solid formulation keeps its physical stability for at least 5 weeks. In one further specific embodiment, the solid formulation keeps its physical stability for at least 10 weeks.

According to one embodiment, the specific surface area (BET) of the solid formulation is higher than the specific surface area of the citric acid and/or saccharin; when the citric acid and/or saccharin is not included in the solid formulation.

In one embodiment, the specific surface area (BET) of the solid formulation is higher than 5 $m^2/g$; preferably higher than 10 $m^2/g$; more preferably higher than 20 $m^2/g$. In one specific embodiment, the specific surface area (BET) of the solid formulation is about 25 $m^2/g$. In one specific embodiment, the specific surface area (BET) of the solid formulation is about 20 $m^2/g$. In one specific embodiment, the specific surface area (BET) of the solid formulation is about 6 $m^2/g$.

According to one embodiment, the solid formulation is not a pharmaceutical composition. In one embodiment, the solid formulation is not an oral formulation such as oral powder. In one embodiment, the solid formulation is not a solid formulation such as a solid tablet. In these embodiments, the solid formulation as such (per se) is not suitable to be directly administrated to a subject for therapeutic purposes, e.g., because it comprises a very high concentration of the therapeutic agent (namely, the 1,2,4-oxadiazole derivative), which would cause toxicity or significant adverse effects or which would not lead to potent medical treatment. However, the solid formulation may be formulated in a pharmaceutical composition as a therapeutic agent for therapeutic purposes, typically in very low amounts, as described hereinafter.

Salts

The invention also relates to a citrate and/or saccharin salt of a 1,2,4-oxadiazole derivative comprising exactly two monocyclic tertiary amine groups.

According to one embodiment, the salt is a mono- or di-citrate salt of the 1,2,4-oxadiazole derivative, i.e., the 1,2,4-oxadiazole derivative is ionized through at least one proton transfer from one citric acid to at least one of the tertiary amine groups. In one embodiment, the salt is a di-citrate salt of the 1,2,4-oxadiazole derivative, i.e., the 1,2,4-oxadiazole derivative is ionized through two proton transfer from one or two citric acid to both tertiary amine groups.

According to one embodiment, the salt is a mono- or di-saccharin salt of the 1,2,4-oxadiazole derivative, i.e., the 1,2,4-oxadiazole derivative is ionized through at least one proton transfer from one saccharin to at least one of the tertiary amine groups. In one embodiment, the salt is a di-saccharin salt of the 1,2,4-oxadiazole derivative, i.e., the 1,2,4-oxadiazole derivative is ionized through two proton transfer from two saccharin to both tertiary amine groups.

In one embodiment, the salt is a mono-citrate and a mono-saccharin salt of the 1,2,4-oxadiazole derivative, i.e., the 1,2,4-oxadiazole derivative is ionized through one proton transfer from one citric acid and one proton transfer from one saccharin to both tertiary amine groups.

According to one embodiment, the salt is a pharmaceutically acceptable salt.

According to one embodiment, the 1,2,4-oxadiazole derivative is of Formula (I-0) or is Compound A, as described hereinabove.

Process and Method

The invention also relates to a process for manufacturing a solid composition according to the invention as described hereinabove, comprising a step of mixing a 1,2,4-oxadiazole derivative comprising exactly two monocyclic tertiary amine groups with citric acid and/or saccharin, wherein the initial molar ratio between the total amount of citric acid and/or saccharin and the amount of the 1,2,4-oxadiazole derivative is higher or equal to about 2.

The invention also relates to a method for increasing the physical stability of a 1,2,4-oxadiazole derivative comprising exactly two monocyclic tertiary amine groups, comprising a step of mixing the 1,2,4-oxadiazole derivative with citric acid and/or saccharin, wherein the initial molar ratio between the total amount of citric acid and/or saccharin and the amount of the 1,2,4-oxadiazole derivative is higher or equal to about 2.

In accordance with the definition of "physical stability" provided hereinabove, in the invention an "improvement of the physical stability" or an "increase of the physical stability" of a substance refers to reduction (or suppression) of deliquescence of the substance and/or to reduction (or suppression) of hygroscopy—so that the substance remains is not deliquescent and/or absorbs less water; and/or to increase of the melting point of the substance—so that the substance becomes solid.

Reduction of deliquescence of a substance may possibly be characterized by a reduction of the hygroscopy of the substance. Hygroscopy may for example be measured by DVS (Dynamic Vapor Sorption), which measures the change in mass of a sample regarding the vapor pressure of a solvent.

Melting point of a substance may for example be measured by DSC (Differential Scanning calorimetry) analysis, which measures the heat flow between the sample and a reference maintained both at the same temperature, or by a melting-point meter, a device where the sample can be observed when it is heated gradually in order to detect the melting point.

According to one embodiment, the 1,2,4-oxadiazole derivative is of Formula (I-0) or is Compound A, as described hereinabove.

According to one embodiment, the initial molar ratio between the total amount of citric acid and/or saccharin and the amount of the 1,2,4-oxadiazole derivative is lower or equal to about 100. In one embodiment, the molar ratio ranges from about 2 to about 20. In one specific embodiment, the molar ratio ranges from about 2 to about 10. In one further specific embodiment, the molar ratio ranges from about 2 to about 5. In one further specific embodiment, the molar ratio is about 2, about 3, about 4 or about 5. In one further specific embodiment, the molar ratio ranges from about 2 to about 3. In one further specific embodiment, the molar ratio is about 2.

According to one embodiment, the process or method comprises a first step of contacting the 1,2,4-oxadiazole derivative with citric acid and/or saccharin followed by a second step of mixing the 1,2,4-oxadiazole derivative and citric acid and/or saccharin.

According to one embodiment, the mixing is stirring. According to one embodiment, the mixing is grinding.

According to one embodiment, no solvent is present during the mixing step. In one embodiment, no substance other than 1,2,4-oxadiazole derivative(s) and citric acid and/or saccharin is present during the mixing step.

Pharmaceutical Composition

The invention also relates to a pharmaceutical composition comprising a solid formulation according to the invention as described hereinabove and at least one pharmaceutically acceptable excipient.

According to one embodiment, the solid formulation in the pharmaceutical composition is a therapeutic agent.

According to one embodiment, the pharmaceutical composition comprises the solid formulation in an amount ranging from about 0.0001% to about 20% w/w, preferably ranging from about 0.001% to about 10% w/w, more preferably ranging from about 0.01% to about 5% w/w. In one embodiment, the pharmaceutical composition comprises the solid formulation in an amount ranging from about 0.01% to about 5% w/w, preferably ranging from about 0.05 to about 2.5% w/w, more preferably ranging from about 0.1 to about 1% w/w. In these embodiments, "w/w" means "in weight of the total weight of the pharmaceutical composition".

According to one embodiment, the at least one pharmaceutically acceptable excipient is free of citric acid. According to one embodiment, the at least one pharmaceutically acceptable excipient is free of saccharin. In one embodiment, the at least one pharmaceutically acceptable excipient is free of citric acid and free of saccharin, i.e., each pharmaceutically acceptable excipient which is comprised in the pharmaceutical composition does not itself comprise citric acid or saccharin.

Uses

The invention also relates to a solid formulation or to a pharmaceutical composition according to the invention as described hereinabove for use as a medicament.

According to one embodiment, the solid formulation or the pharmaceutical composition is for use in the treatment and/or prevention of a disease in which GLP-1 receptor participates or mediates.

According to one embodiment, the solid formulation or the pharmaceutical composition is for use in the treatment and/or prevention of a disease wherein a GLP-1 receptor participates or mediates as disclosed in WO 2012/101292 A1 patent application (VIVIABIOTECH SL).

In one embodiment, the disease wherein a GLP-1 receptor participates or mediates is selected from obesity, anorexia, lipid dysfunction, diabetes, hyperinsulinism and metabolic syndrome. In one embodiment, the disease wherein GLP-1 receptor participates or mediates is obesity. In another embodiment, the disease wherein GLP-1 receptor participates or mediates is diabetes. In one embodiment, diabetes is type 2 Mellitus diabetes.

In one embodiment, the disease wherein a GLP-1 receptor participates or mediates is selected from diseases induced by or associated with obesity, anorexia, lipid dysfunction, diabetes, hyperinsulinism and metabolic syndrome ("GLP-1-related disease"). In one embodiment, the disease is induced by or associated with diabetes ("diabetes-related disease"), such as diabetic neuropathy, diabetic retinopathy, glaucoma, cataract, diabetic nephropathy or diabetic foot ulcer.

According to one embodiment, the solid formulation or the pharmaceutical composition is for use in the treatment and/or prevention of eating disorders. In one embodiment, the eating disorder is selected from obesity, anorexia, lipid dysfunction, diabetes, hyperinsulinism and metabolic syndrome.

According to one embodiment, the solid formulation or the pharmaceutical composition is for use in the treatment and/or prevention of metabolic disorders such as diabetes or obesity. In one embodiment, the metabolic disorder is selected from diabetes and obesity.

According to one embodiment, the solid formulation or the pharmaceutical composition is for use in the treatment and/or prevention of cardiovascular diseases. In one embodiment, the cardiovascular disease is selected from coronary artery diseases, stroke, heart failure, hypertensive heart disease and congenital heart disease.

According to one embodiment, the solid formulation or the pharmaceutical composition is for use in the treatment and/or prevention of neurodegenerative diseases. In one embodiment, the neurodegenerative disease is selected from Alzheimer's disease, Parkinson's disease, multiple system atrophy, Huntington's disease, optic nerve degeneration and movement disorder, neuromuscular disorders and cognitive deficiency.

According to one embodiment, the solid formulation or the pharmaceutical composition is for use in the treatment and/or prevention of neurological or neuropsychiatric diseases. In one embodiment, the neurological or neuropsychiatric disease is selected from epilepsy, schizophrenia, bipolar disorders, depression and pain.

The invention thus also relates to methods of treatment and/or prevention of diseases, comprising the administration of a therapeutically effective amount of a solid formulation or pharmaceutical composition according to the invention, as described hereinabove, to a subject in need thereof. The invention thus also relates to the use of a solid formulation or pharmaceutical composition according to the invention, as described hereinabove, in the manufacture of a medicament.

The invention also relates to a non-therapeutic method of prevention of weight gain in a subject, comprising a step of administration to said subject of a solid formulation or pharmaceutical composition according to the invention, as described hereinabove. According to one embodiment, prevention of weight gain is prevention of fat gain.

The invention also relates to a non-therapeutic method of control of weight gain in a subject, comprising a step of administration to said subject of a solid formulation or pharmaceutical composition according to the invention, as described hereinabove. According to one embodiment, control of weight gain is control of fat gain.

The invention also relates to a non-therapeutic method of stimulation of weight loss in a subject, comprising a step of administration to said subject of a solid formulation or pharmaceutical composition according to the invention, as described hereinabove.

According to one embodiment, stimulation of weight loss is stimulation of fat loss.

EXAMPLES

The present invention is further illustrated by the following examples.

Example 1

Synthesis of Solid Formulations

Materials

Compound A was synthetized according to methods known in the art. $^{13}$C-NMR (CDC13): δ 24.5 ($CH_{2pip}$), 28.3 ($CH_{2pip}$), 32.6 (CH), 52.7 ($CH_{2pip}$), 53.2 ($CH_2N_{pip}$), 53.7 ($2CH_2N_{morph}$), 57.6 ($CH_2N_{pip}$), 62.3 ($CH_{2morph}$), 66.2 ($2CH_2O_{morph}$), 122.4 (q, CF3), 125.2 (q, C) 126.2 (2CH), 127.9 (2CH), 130.9 (q, C)166.5 (C(N)═N), 177.8 (C(O)═N). $^1$H-NMR ($CDCl_3$): δ 0.88-1.01 (m, 1H, 1/2$CH_{2pip}$), 1.58-1.80 (m, 3H, ½ $CH_{2pip}$, $CH_{2pip}$), 1.87-2.02 (m, 2H, ½ $CH_2N_{pip}$, CH), 2.13-2.28 (m, 3H, $CH_2$morph, ½ $CH_2N_{pip}$), 2.32-2.54 (m, 4H, $2CH_2N_{morph}$), 2.92 (d, 1H, ½ $CH_2N_{pip}$), 3.09 (d, 1H, 1/2$CH_2N_{pip}$), 3.62-3.78 (m, 4H, $2CH_2O_{morph}$), 3.94 (q, 2H, $CH_{2pip}$), 7.75 (d, 2H, 2CHAr), 8.23 (d, 2H, 2CHAr). Rf: 0.67 (thin layer chromatography (TLC) on silica plate (silica gel 60 F254 Merck on aluminum foil of 2 mm thickness) with eluent: dichloromethane/methanol (9/1), reveled by UV and KMnO4 solution).

All others reactants and all solvents were purchased from commercial providers. All reactants and solvents used were reagent grade.

Example 1-1

Mixing A with Liquid Acids

General Procedure

In a round bottom flask, to a solution of A in anhydrous Et2O (6 mL/mmol) under argon atmosphere, the acid was added dropwise, as a pure liquid or in anhydrous Et2O (3 mL/mmol) solution. The mixture was allowed to stand for 3 h. The product was then isolated by evaporation of the solvent and was dried under vacuum.

Acetic Acid

The reaction between A and acetic acid was performed with 2.0 equivalents of the acid. After drying under vacuum a sticky oil was obtained.

Hydrobromic Acid

The reaction between A and hydrobromic acid was performed with 2.0 equivalents of the acid. After drying under vacuum a deliquescent solid was obtained.

Hydrochloric Acid

The reaction between A and hydrochloric acid was performed with a significant excess of the acid. After drying under vacuum a deliquescent solid was obtained.

Methanesulfonic acid

The reaction between A and methanesulfonic acid was performed several times, with 1.0, 1.3, 2.3 and 3.2 equivalents of the acid.

After drying under vacuum a sticky oil was obtained, except for the product formed with 3.2 equivalent which was instead a deliquescent solid.

Sulfuric Acid

The reaction between A and sulfuric acid was performed with 2.0 equivalents of the acid. After drying under vacuum a sticky oil was obtained.

Example 1-2

Mixing A with Solid Acids

General Procedure

Mechanochemistry may be used for efficiently manufacture salts of organic compounds from solid acids or bases. It is a solvent-free process comprising a mixing step such as a grinding step. Grinding step may carried out either by net grinding or "Liquid Assisted Grinding (LAG)" where a very small amount of solvent is added in order to increase the molecular mobility. This aims in accelerating and/or completing the reaction.

In the present case, net grinding was used because Compound A is an oil so that molecular mobility was likely to be sufficient. Two different net grinding procedures were used:

- Solid mixing 1: In an Eppendorf, A (200 mg, 0.5 mmol) and the acid were added. The Eppendorf was then placed in the grinding device (Retsch MM400) and allowed to stir for 90 min at 30 Hz.
- Solid mixing 2: In a mortar, A (200 mg, 0.5 mmol) and acid were added and then manually grinded with a pestle.

Citric Acid

The reaction between A and citric acid was performed with 2.0 equivalents of the acid. After grinding, a white powder was obtained ("A-2CA", shown on FIG. 1).

The reaction between A and citric acid was also performed with 1.0 equivalent of the acid. After grinding, a sticky oil was obtained ("A-1CA").

Fumaric Acid

The reaction between A and fumaric acid was performed two times, with 1.0 or 2.0 equivalents of the acid. In both cases, a sticky oil was obtained.

Saccharin

Figure 2:
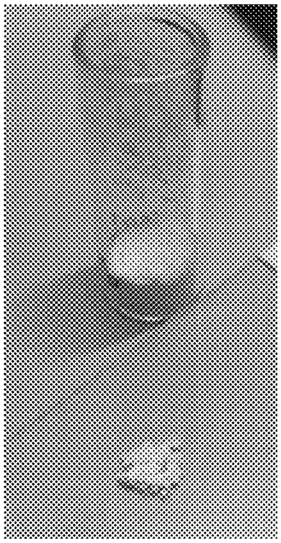
FIG. 2 is a photograph showing A-2SA as a physically stable white powder, obtained by grinding Compound A with 2.0 equivalents of saccharin.

The reaction between A and saccharin was performed two times, with 1.0 or 2.0 equivalents of the acid. When only one equivalent of saccharin was used, a sticky oil was obtained. On the other hand, with two equivalents a white powder was obtained ("A-2SA", shown on FIG. 2).

Saccharin and Citric Acid

Figure 3:
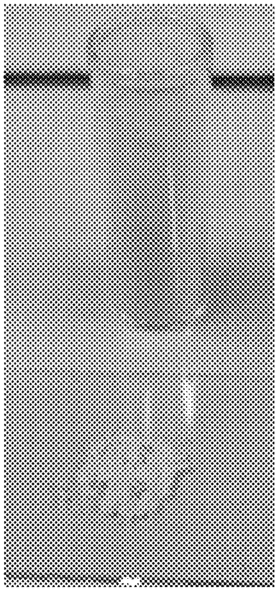
FIG. 3 is a photograph showing A-1CA-1SA as a physically stable white powder, obtained by grinding Compound A with 1.0 equivalent of saccharin and 1.0 equivalent of citric acid.

The reaction between A, saccharin and citric acid was performed with 1.0 equivalent of each of the acids. After grinding, a white powder was obtained ("A-1CA-1SA", shown on FIG. 3).

Sodium Bicarbonate

The reaction between A and sodium bicarbonate was performed two times, with 1.0 or 2.0 equivalents of the acid. In both cases, a sticky oil was obtained.

Succinic Acid

The reaction between A and succinic acid was performed two times, with 1.0 or 2.0 equivalents of the acid. In both cases, a sticky oil was obtained.

Example 2

Analysis of Solid Formulations

Material and Methods

Nuclear Magnetic Resonance (NMR) Analysis

NMR Spectra were recorded on a JEOL JNM EX-400 400 Hz or JEOL JNM-ECZ 500 Hz. Samples were prepared in deuterated DMSO at room temperature in standard quartz tubes (5 mm). The spectra were analysed with Delta program.

Brunauer, Emmett and Teller (BET) Analysis

Specific surface area was measured by Nitrogen adsorption-desorption analyses at 77 K with a volumetric adsorption analyser (Micromeritics 3Flex physisorption apparatus). The Brunauer—Emmet—Teller (BET) method was applied in the 0.05-0.20 P /PO range to calculate the specific surface area.

X-Ray Powder Diffraction (PXRD) Analysis

X-Ray powder diffraction (PXRD) data were collected on a Panalytical X' Pert Pro diffractometer (Bragg—Brentano geometry, X' Celerator detector), using Cu Ka radiation=1.54184 A) at 45 kV and 30 mA. Each sample was analysed between 4 and 50° in 2θ.

Scanning Electron Microscopy (SEM) Pictures

Pictures of the samples were taken with a SEM microscope Jeol JSM-601OLV with a SEI detector.

Example 2-1

A-2CA Analysis 2-1-1) Manufacture of A-2CA Analytical Sample

In a 2 mL Eppendorf tube, A (201 mg, 0.490 mmol, 1.0 eq), citric acid (188 mg, 0.976 mmol, 2.0 eq), two of 3 mm and five of 2 mm stainless steel grinding balls were added. The Eppendorf was then placed in a grinding machine (Retsch Mixer Mill 400), equipped with two grinding jars. The dry grinding was then performed for 90 min at 30 Hz. Similar results were obtained by decreasing grinding time to 30 min In order to improve the stirring, the reaction mixture was placed in a mortar and was manually ground with a pestle until A-2CA as a white powder was obtained.

2-1-2) NMR Analysis $^{1}H$ NMR of A-2CA showed a spectrum similar to a superposition of the spectra of A and citric acid. Therefore, the molecular structure of A and citric acid have been maintained and no deterioration of the reactants has been observed.

$^{13}C$ NMR of A-2CA showed no significant shift for the carbon atoms near the nitrogen atoms (tertiary amines) in comparison with A. Thus, it cannot be assessed from RMN whether a salt has been formed.

2-1-3) Deliquescence Test

A-2CA was left to the air at room temperature (19±2° C.) with normal humidity (relative humidity 60±5%) for 12 days.

No liquid phase appeared over this period, A-2CA solid composition is thus physically stable.

After 7 days, A-2CA powder particles became slightly stickier, the solid composition may thus be moderately hygroscopic.

2-1-4) Powder XRD

Figure 4:
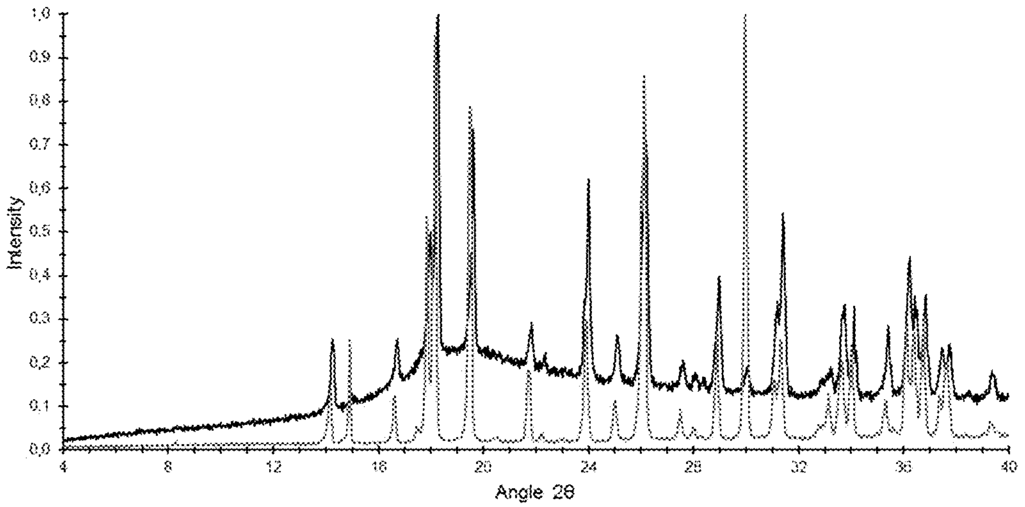
FIG. 4 is a graph showing the superposed powder XRD diffractograms of A-2CA solid formulation (black curve above) and citric acid (grey curve below FIG. 5 is a photograph showing a SEM microscopy picture of A-2CA solid formulation.

The diffractograms of A-2CA and citric acid are shown on FIG. 4. Citric acid is detected in A-2CA as both diffractogram present the same peak patterns. The diffractogram of A-2CA additionally shows the presence of an amorphous phase.

2-1-5) Specific Surface Area (BET)

The specific surface area of a A-2CA sample was measured by BET analysis as:

BET surface $_{A-2CA}$=26.6 $m^2/g$.

2-1-6) SEM Pictures

Figure 5:
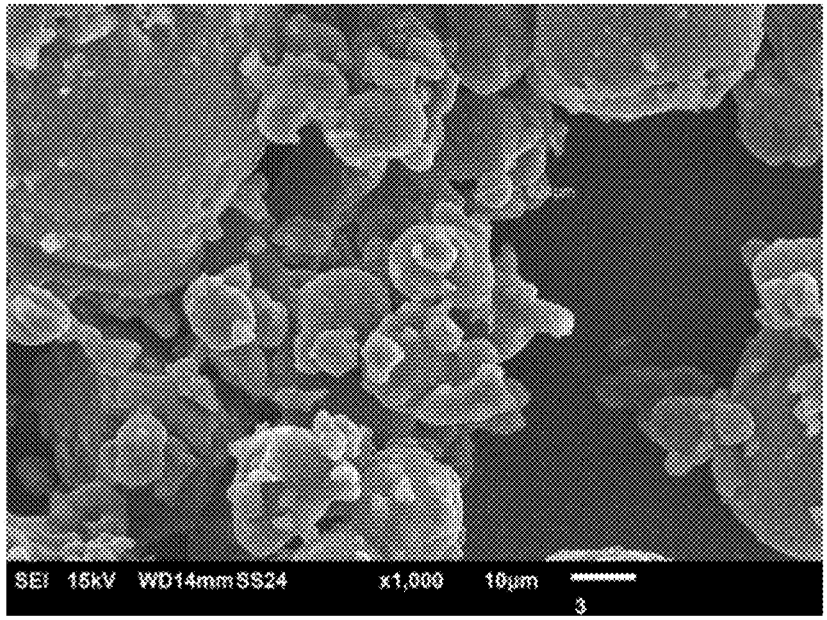

Many SEM pictures of a A-2CA sample were recorded, a representative example being shown on FIG. 5. SEM pictures may be useful in order to characterize the particle size distribution in the solid formulation.

Example 2-2

A-2SA Analysis 2-2-1) Manufacture of A-2SA Analytical Sample

In a 2 mL Eppendorf tube, A (150 mg, 0.365 mmol, 1.0 eq), saccharin (135 mg, 0.737 mmol, 2.0 eq), two of 3 mm and five of 2 mm stainless steel grinding balls were added. The Eppendorf was then placed in the grinding machine (Retsch Mixer Mill 400), equipped with two grinding jars. The dry grinding was then performed from 35 to 90 min at 30 Hz to afford A-2SA as a white powder.

It was found that the grinding time did not affect the results. The following analyses were performed on the solid formulation obtained after 35 min of grinding.

2-2-2) NMR Analysis $^{1}H$ NMR of A-2SA showed a spectrum similar to a superposition of the spectra of A and saccharin. Therefore, the molecular structure of A and saccharin have been maintained and no deterioration of the reactants has been observed.

$^{13}C$ NMR of A-2SA showed no significant shift for the carbon atoms near the nitrogen atoms (tertiary amines) in comparison with A. Thus, it cannot be assessed from RMN whether a salt has been formed.

2-2-3) Deliquescence Test

A-2SA was left to the air at room temperature (19±2° C.) with normal humidity (relative humidity 60±5%) for 12 days.

No liquid phase appeared over this period, A-2SA solid composition is thus physically stable.

After 7 days, A-2SA powder particles became slightly stickier, the solid composition may thus be moderately hygroscopic.

2-2-4) Powder XRD

Comparative analysis — Powder XRD and SEM pictures of saccharin

For comparison purpose it was relevant to observe the effect of grinding on saccharin. Commercial saccharin was grinded for 35 min at 30 Hz and was compared to a non-grinded powder from the same batch of commercial saccharin.

The diffraction pattern (PXRD) of saccharin before and after grinding were obtained and compared: they are identical. Therefore, grinding does not lead to amorphization of saccharin under the experimental conditions.

Moreover, Scanning Electron Microscopy (SEM) pictures of saccharin before and after grinding confirmed that the crystal structure of grinded saccharin does not change, although it has smaller particles than commercial saccharin.

Powder XRD of A-2SA

Figure 6:
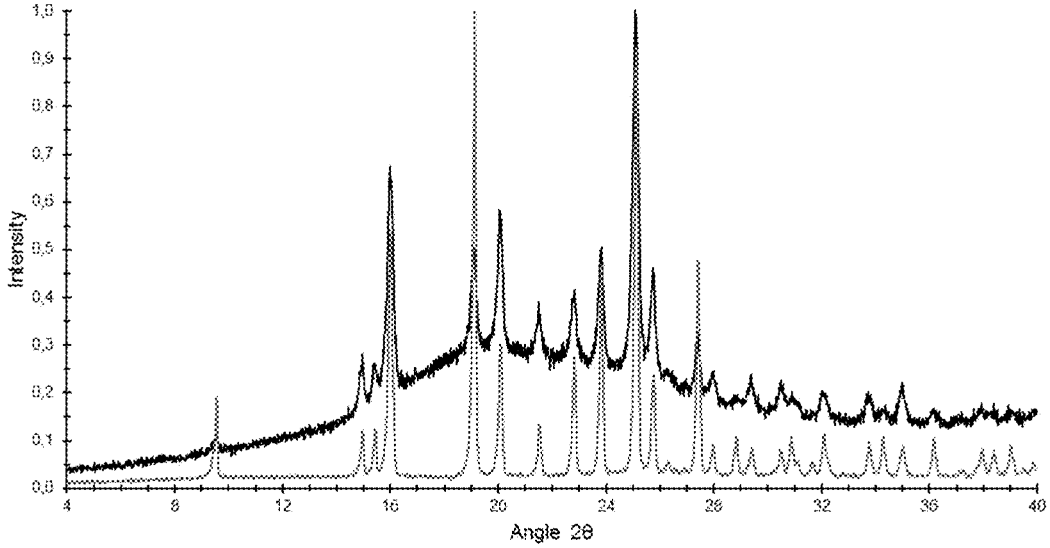
FIG. 6 is a graph showing the superposed powder XRD diffractograms of A-2SA solid formulation (black curve above) and saccharin (grey curve below).

The diffractograms of A-2SA and saccharin are shown on FIG. 6. As for A-2CA, saccharin is detected in A-2SA as both diffractogram present the same peak patterns. The diffractogram of A-2SA additionally shows the presence of an amorphous phase.

2-2-5) Specific surface area

Comparative analysis — Specific Surface Area of Saccharin

For comparison purpose, it was relevant to observe the effect of grinding on saccharin. Commercial saccharin was grinded for 35 min at 30 Hz and was compared to a non-grinded powder from the same batch of commercial saccharin.

The specific surface area of the two saccharin samples was measured by BET analysis as:

Saccharin (commercial): BET surface SA(c)=9.9 $m^2/g$.

Saccharin (after grinding): BET surface SA($_g$)=6.7 $m^2/g$.

This experiment evidence that no significant change is observed regarding the specific surface area (BET) of saccharin after grinding, with only a moderate decrease (about −30%).

A-2SA specific surface area

The specific surface area of a A-2SA sample was measured by BET analysis as:

BET surface A-2SA=21.6 m2/g.

A significant change was observed regarding the specific surface area (BET) of saccharin mixed with A-2SA which is three times higher than the one of saccharin alone (about +220%), following the same grinding procedure.

Therefore, the presence of A in the solid formulation modify significantly the specific surface area of the solid, thereby evidencing an interaction between the two compounds of the solid formulation. The solid formulation is thus not a mere admixture.

2-2-6) SEM Pictures

Figure 7:
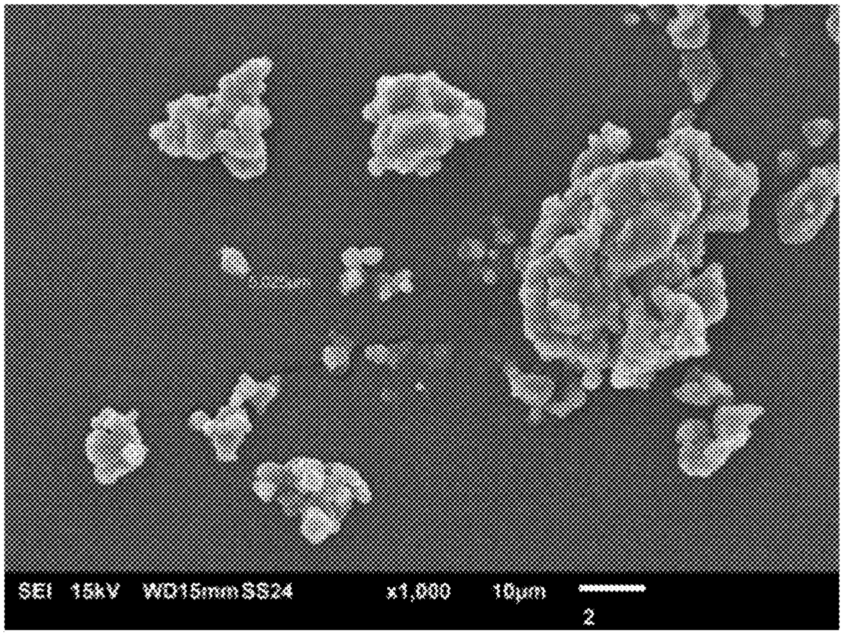
FIG. 7 is a photograph showing a SEM microscopy picture of A-2SA solid formulation.

Many SEM pictures of a A-2SA sample were recorded, a representative example being shown on FIG. 7.

Example 2-3

A-ICA-ISA Analysis 2-3-1) Manufacture of A-1CA-1SA Analytical Sample

In a grinding jar, A (302 mg, 0.735 mmol, 1.0 eq), citric acid (142 mg, 0.742 mmol, 1.0 eq), saccharin (13 mg, 0.737 mmol, 1.0 eq) and a grinding ball made of agate were added. The jar was then placed in the grinding machine (Retsch Mixer Mill 400), equipped with another grinding jars. The dry grinding was performed for 60 min at 30 Hz to afford A-1CA-1SA as a white solid.

2-3-2) NMR Analysis $^1$H NMR of A-1CA-1SA showed a spectrum similar to a superposition of the spectra of A and citric acid and saccharin. Therefore, the molecular structure of A, citric acid and saccharin has been maintained and no deterioration of the reactants has been observed.

$^{13}$C NMR of A-1CA-1SA showed no significant shift for the carbon atoms near the nitrogen atoms (tertiary amines) in comparison with A. Thus, it cannot be assessed from RMN whether a salt has been formed.

2-3-3) Deliquescence Test

A-1CA-1SA was left to the air at room temperature (19±2° C.) with normal humidity (relative humidity 60±5%) for 30 days.

No liquid phase appeared over this period, A-1CA-1SA solid composition is thus physically stable.

3-3-4) Powder XRD

Figure 8:
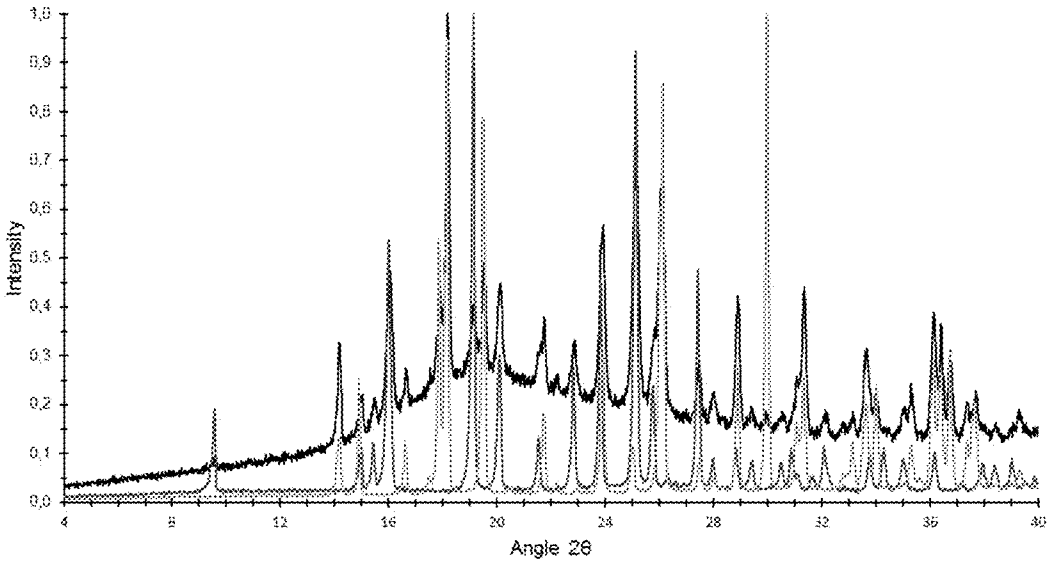
FIG. 8 is a graph showing the superposed powder XRD diffractograms of A-1CA-1SA solid formulation (black curve above), saccharin (dark grey curve below) and citric acid (pale grey curve below).

The diffractograms of A-1CA-1SA, citric acid and saccharin are shown on FIG. 8. As for A-2CA and A-2SA, citric acid and saccharin are detected in A-1CA-1SA as both diffractogram present the same peak patterns. The diffractogram of A-1CA-1SA additionally shows the presence of an amorphous phase.

3-3-5) Specific Surface Area

The specific surface area of A-1CA-1SA sample was measured by BET analysis as: BET surface A-1CA-1SA=6.5 $m^2/g$.

3-3-6) SEM Pictures

Figure 9:
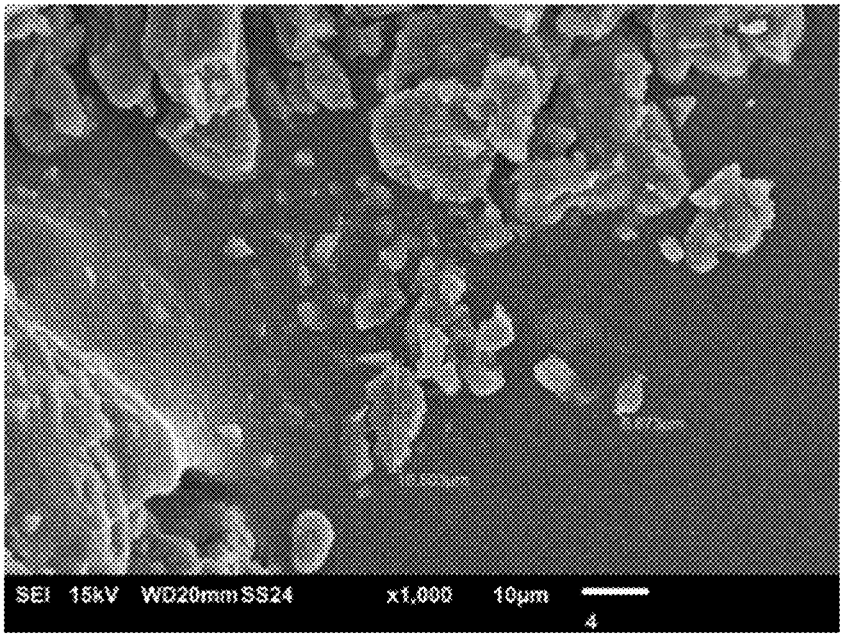
FIG. 9 is a photograph showing a SEM microscopy picture of A-1CA-1SA solid formulation.

Many SEM pictures of a A-1CA-1SA sample were recorded, a representative example being shown on FIG. 9.

CONCLUSION

Due to the presence of two tertiary amine functions in the 1,2,4-oxadiazole derivative A, the manufacture of mono- or di-addition salts have been considered in order to obtain a physically stable form of the active ingredient.

The results of the in-depth formulation study carried out by the Applicant (Example 1) can be summarized as shown in Table 1 below.

TABLE 1

| Acid | Resulting composition | Stability |
|---|---|---|
| Acetic acid (2 eq.) | Sticky oil | NO |
| Hydrobromic acid (2 eq.) | Hygroscopic compound | NO |
| Hydrochloric acid (excess) | Hygroscopic compound | NO |
| Methanesulfonic acid (1 to 3.2 eq.) | Hygroscopic compound | NO |
| Sulfuric acid (2 eq.) | Sticky oil | NO |
| Citric acid (1 eq.) | Sticky oil | NO |
| Citric acid (2 eq.) | White solid | YES |
| Fumaric acid (1 or 2 eq.) | Sticky oil | NO |
| Saccharin (1 eq.) | Sticky oil | NO |
| Saccharin (2 eq.) | White solid | YES |
| Saccharin (1 eq.) + Citric acid (1 eq.) | White solid | YES |
| Sodium bicarbonate (1 or 2 eq.) | Sticky oil | NO |
| Succinic acid (1 or 2 eq.) | Sticky oil | NO |

With most of the acids, used as liquids or solids in various relative amounts to A, led to the formation of either sticky oil or deliquescent (hygroscopic) compounds. Therefore, it appeared that physically stable addition salts of compound A cannot be easily obtained.

However, the use of specific acids being citric acid and/or saccharin has unexpectedly led to a stable solid formulation of compound A. It was also found that citric acid and/or saccharin had to be used in an amount of at least two equivalents in order to achieve the stabilization effect: when only one equivalent of citric acid or saccharin is added to compound A, then the resulting mixture is a sticky oil.

Analytical studies (Example 2) have confirmed that the solid formulation according to the invention is physically stable.

It was also evidenced that the main structure of compound A in a solid formulation according to the invention is not affected, so that it can reasonably be expected that its biological activity will be comparable with the one of "free" compound A.

Significant surface specific area increase observed for A-2SA further shows that the solid composition is not a mere admixture but that A and saccharin have a chemical interaction within the solid formulation.

Without wishing to be bound by any theory, the Applicant believes that compound A might be associated with citric acid and/or saccharin by means of non-covalent bonds ("weak" bonds), e.g., hydrogen bonds or Van der Waals interactions. In that case, the solid formulation would then be a multi-component complex wherein A and citric acid and/or saccharin are weakly associated without actual proton transfer, although with sufficient interaction to increase significantly the physical stability of compound A.

In conclusion, the presently provided experimental results unambiguously evidence that the invention allows a fast and easy physical stabilisation of 1,2,4-oxadiazole derivatives, by means of mixing it with citric acid and/or saccharin. Citric acid or saccharin are thus potent stabilizing agents for 1,2,4-oxadiazole derivatives with two tertiary amines functions, alone or in combination. The physically stable solid powder obtained render 1,2,4-oxadiazole derivatives more useful for industrial applications and/or as components of a medicament.

The invention claimed is:

1. A solid formulation in the form of a powder comprising from about 85% to about 100% w/w of the di-citrate salt of 4-((1-((3-(4-(trifluoromethyl)phenyl-1,2,4-oxadiazol-5-yl) methyl)piperidin-3-yl)methyl)morpholine.

2. The solid formulation according to claim 1, comprising from about 90% to about 100% w/w of the di-citrate salt of 4-((1-((3-(4-(trifluoromethyl)phenyl-1,2,4-oxadiazol-5-yl) methyl)piperidin-3-yl)methyl)morpholine.

3. The solid formulation according to claim 2, comprising from about 95% to about 100% w/w of the di-citrate salt of 4-((1-((3-(4-(trifluoromethyl)phenyl-1,2,4-oxadiazol-5-yl) methyl)piperidin-3-yl)methyl)morpholine.

4. A pharmaceutical composition comprising the solid formulation according to claim 1 and at least one pharmaceutically acceptable excipient, wherein said at least one pharmaceutically acceptable excipient is free of citric acid and free of saccharin.

5. The pharmaceutical composition according to claim 4, comprising said solid formulation in an amount ranging from about 0.01% to about 5% w/w based on the total weight of the pharmaceutical composition.

6. A solid formulation in the form of a powder comprising from about 85% to about 100% w/w of the di-saccharine salt of 4-((1-((3-(4-(trifluoromethyl)phenyl-1,2,4-oxadiazol-5-yl)methyl)piperidin-3-yl)methyl)morpholine.

7. The solid formulation according to claim 6, comprising from about 90% to about 100% w/w of the di-saccharine salt of 4-((1-((3-(4-(trifluoromethyl)phenyl-1,2,4-oxadiazol-5-yl)methyl)piperidin-3-yl)methyl)morpholine.

8. The solid formulation according to claim 7, comprising from about 95% to about 100% w/w of the di-saccharine salt of 4-((1-((3-(4-(trifluoromethyl)phenyl-1,2,4-oxadiazol-5-yl)methyl)piperidin-3-yl)methyl)morpholine.

9. A pharmaceutical composition comprising the solid formulation according to claim 6 and at least one pharmaceutically acceptable excipient, wherein said at least one pharmaceutically acceptable excipient is free of citric acid and free of saccharin.

10. The pharmaceutical composition according to claim 9, comprising said solid formulation in an amount ranging from about 0.01% to about 5% w/w based on the total weight of the pharmaceutical composition.

11. A solid formulation in the form of a powder comprising from about 85% to about 100% w/w of the mono-citrate, mono-saccharine salt of 4-((1-((3-(4-(trifluoromethyl)phenyl-1,2,4-oxadiazol-5-yl)methyl)piperidin-3-yl)methyl)morpholine.

12. The solid formulation according to claim 11, comprising from about 90% to about 100% w/w of the mono-citrate, mono-saccharine salt of 4-((1-((3-(4-(trifluoromethyl)phenyl-1,2,4-oxadiazol-5-yl)methyl)piperidin-3-yl)methyl)morpholine.

13. The solid formulation according to claim 12, comprising from about 95% to about 100% w/w of the di-saccharine salt of the mono-citrate, mono-saccharine salt of 4-((1-((3-(4-(trifluoromethyl)phenyl-1,2,4-oxadiazol-5-yl)methyl)piperidin-3-yl) methyl)morpholine.

14. A pharmaceutical composition comprising the solid formulation according to claim 11 and at least one pharmaceutically acceptable excipient, wherein said at least one pharmaceutically acceptable excipient is free of citric acid and free of saccharin.

15. The pharmaceutical composition according to claim 14, comprising said solid formulation in an amount ranging from about 0.01% to about 5% w/w based on the total weight of the pharmaceutical composition.

16. A solid formulation in the form of a powder comprising from about 85% to about 100% w/w of a mixture of salts selected from the group consisting of the di-citrate salt of 4-((1-((3-(4-(trifluoromethyl)phenyl-1,2,4-oxadiazol-5-yl) methyl)piperidin-3-yl) methyl) morpholine;

the di-saccharine salt of 4-((1-((3-(4-(trifluoromethyl) phenyl-1,2,4-oxadiazol-5-yl)methyl)piperidin-3-yl) methyl)morpholine; and the mono-citrate, mono-saccharine salt of 4-((1-((3-(4-(trifluoromethyl) phenyl-1,2,4-oxadiazol-5-yl) methyl) piperidin-3-yl)methyl)morpholine.

17. The solid formulation according to claim 16, comprising from about 90% to about 100% w/w of said mixture of salts.

18. The solid formulation according to claim 17, comprising from about 95% to about 100% w/w of said mixture of salts.

19. A pharmaceutical composition comprising the solid formulation according to claim 16 and at least one pharmaceutically acceptable excipient, wherein said at least one pharmaceutically acceptable excipient is free of citric acid and free of saccharin.

20. The pharmaceutical composition according to claim 19, comprising said solid formulation in an amount ranging from about 0.01% to about 5% w/w based on the total weight of the pharmaceutical composition.

* * * * *